(12) United States Patent
Yarussi (10) Patent No.: US 8,259,297 B1
(45) Date of Patent: Sep. 4, 2012

(54) SCANNING FOCAL LENGTH METROLOGY

(75) Inventor: Richard A. Yarussi, San Francisco, CA (US)

(73) Assignee: Nanometrics Incorporated, Milpitas, CA (US)

( * ) Notice: Subject to any disclaimer, the term of this patent is extended or adjusted under 35 U.S.C. 154(b) by 22 days.

(21) Appl. No.: 13/074,774

(22) Filed: Mar. 29, 2011

Related U.S. Application Data (63) Continuation-in-part of application No. 12/750,577, filed on Mar. 30, 2010, which is a continuation of application No. 11/624,182, filed on Jan. 17, 2007, now Pat. No. 7,697,135.

(60) Provisional application No. 61/319,212, filed on Mar. 30, 2010, provisional application No. 60/779,176, filed on Mar. 3, 2006.

(51) Int. Cl.
G01J 3/28 (2006.01)

(52) U.S. Cl. .................................................. 356/326

(58) Field of Classification Search .................. 356/328, 356/326
See application file for complete search history.

(56) References Cited

U.S. PATENT DOCUMENTS

| | | | |
|---|---|---|---|
| 7,663,748 B2 * | 2/2010 | Van Beek et al. ............. | 356/317 |
| 7,697,135 B1 | 4/2010 | Yarussi et al. | |
| 2005/0092930 A1 | 5/2005 | Watanabe et al. | |
| 2005/0280818 A1 | 12/2005 | Yamashita et al. | |
| 2006/0038980 A1 | 2/2006 | Naka et al. | |
| 2009/0161104 A1 * | 6/2009 | Schultz et al. ................ | 356/317 |

OTHER PUBLICATIONS

An-Shun Liu, et al., "Image-based Nano-scale Dimensional Metrology", Proc. SPIE 6152, pp. 61522G1-6152G10 (Mar. 24, 2006).
Office Action mailed by Examiner Abdullahi Nur on Nov. 26, 2008 for U.S. Appl. No. 11/624,182, filed Jan. 17, 2007, by Yarussi et al., (13 pgs).
Response to Office Action dated Feb. 25, 2009 for U.S. Appl. No. 11/624,182, filed Jan. 17, 2007, by Yarussi et al., (10 pgs).
Office Action mailed by Examiner Abdullahi Nur on Jun. 11, 2009 for U.S. Appl. No. 11/624,182, filed Jan. 17, 2007, by Yarussi et al., (11 pgs).
Response to Office Action dated Sep. 8, 2009 for U.S. Appl. No. 11/624,182, filed Jan. 17, 2007, by Yarussi et al., (11 pgs).
Applicant' Interview Summary dated Dec. 1, 2009 for U.S. Appl. No. 11/624,182, filed Jan. 17, 2007, by Yarussi et al., (2 pgs).
Notice of Allowance mailed by Examiner Abdullahi Nur on Nov. 30, 2009 for U.S. Appl. No. 11/624,182, filed Jan. 17, 2007, by Yarussi et al., (11 pgs).
Office Action mailed Examiner Abdullahi Nur on Aug. 20, 2010 for U.S. Appl. No. 12/750,577, filed Mar. 30, 2010, by Yarussi et al., (9 pgs).
Response to Office Action dated Nov. 18, 2010 for U.S. Appl. No. 12/750,577, filed Mar. 30, 2010, by Yarussi et al., (9 pgs).

(Continued)

*Primary Examiner* — Tarifur Chowdhury
*Assistant Examiner* — Abdullahi Nur
(74) *Attorney, Agent, or Firm* — Silicon Valley Patent Group LLP (57) ABSTRACT

An optical metrology system collects data while scanning over the focal range. The data is evaluated to determine a peak intensity value from the data. In one embodiment, only data from one side of the peak value is used. The characteristic of the sample is determined based on the peak value. In one embodiment, monochromatic light is used. In another embodiment, polychromatic light is used and peak intensity values for a plurality of wavelengths are determine and combined to form a measured spectrum for the sample, which can then be used to determine the sample properties of interest. In one embodiment, the peak intensity is determined using curve fitting.

21 Claims, 7 Drawing Sheets

OTHER PUBLICATIONS

Office Action mailed by Examiner Abdullahi Nur on Feb. 3, 2011 for U.S. Appl. No. 12/750,577, filed Mar. 30, 2010, by Yarussi et al., (9 pgs).

Response to Office Action with filing CPA/RCE dated May 3, 2011 for U.S. Appl. No. 12/750,577, filed Mar. 30, 2010 by Yarussi et al., (16 pages).

Office Action mailed by Examiner Abdullahi Nur on May 26, 2011 for U.S. Appl. No. 12/750,577, filed Mar. 30, 2010 by Yarussi et al., (11 pages).

Response to Office Action dated Aug. 24, 2011 for U.S. Appl. No. 12/750,577, filed Mar. 30, 2010 by Yarussi et al., (9 pages).

Office Action mailed by Examiner Abdullahi Nur on Nov. 14, 2011 for U.S. Appl. No. 12/750,577, filed Mar. 30, 2010 by Yarussi et al., (8 pages).

* cited by examiner

SCANNING FOCAL LENGTH METROLOGY

CROSS-REFERENCE TO RELATED APPLICATION

This application claims the benefit of U.S. Provisional Application No. 61/319,212, filed Mar. 30, 2010, the entirety of which is incorporated herein by reference; and this application is a continuation-in-part application of U.S. patent application Ser. No. 12/750,577 filed Mar. 30, 2010, entitled "Scanning Focal Length Metrology", which is a continuation of U.S. patent application Ser. No. 11/624,182, filed Jan. 17, 2007, and issued as U.S. Pat. No. 7,697,135 on Apr. 13, 2010, which claimed the benefit of Provisional Application No. 60/779,176, filed Mar. 3, 2006, entitled "Scanning Focal Length Metrology" all of which are incorporated by reference herein in their entireties.

FIELD OF THE INVENTION

The present invention is related to optical metrology and, in particular, to a method and apparatus for collecting optical data from a spectral range with a varying focal length.

BACKGROUND

Optical metrology systems, such as reflectometers, often use refractive optics to focus the radiation onto the sample being measured. With the sample positioned in the focal plane of the optical metrology system, the metrology system can measure the desired parameters of the sample, including, but not limited to such things as the thickness and optical characteristics of the film or films on the sample, as well as critical dimensions (CD). Accordingly, prior to measuring a sample, optical metrology systems generally attempt to place the sample at the focal plane of the optical system. Imprecision in the focusing process contributes to a decrease in the precision and repeatability of the measurement results. In the case of measurement systems that use multiple wavelengths of light, refractive focusing optics will intrinsically produce a variation in actual focal length as a function of wavelength. Conventional measurements at a single (e.g. average) focal plane in a multiple wavelength system causes a significant number of wavelengths to be slightly out of focus, resulting in increased spot size and decreased intensity. Thus, improvements are desired.

SUMMARY

In accordance with an embodiment of the present invention, an optical metrology system collects data while scanning over the focal range. The data is evaluated to determine a peak intensity value from the data. In one embodiment, only data from one side of the peak value is used. The characteristic of the sample is determined based on the peak value. In one embodiment, monochromatic light is used. In another embodiment, polychromatic light is used and peak intensity values for a plurality of wavelengths are determine and combined to form a measured spectrum for the sample, which can then be used to determine the sample properties of interest. In one embodiment, the peak intensity is determined using curve fitting.

DETAILED DESCRIPTION

Figure 1:
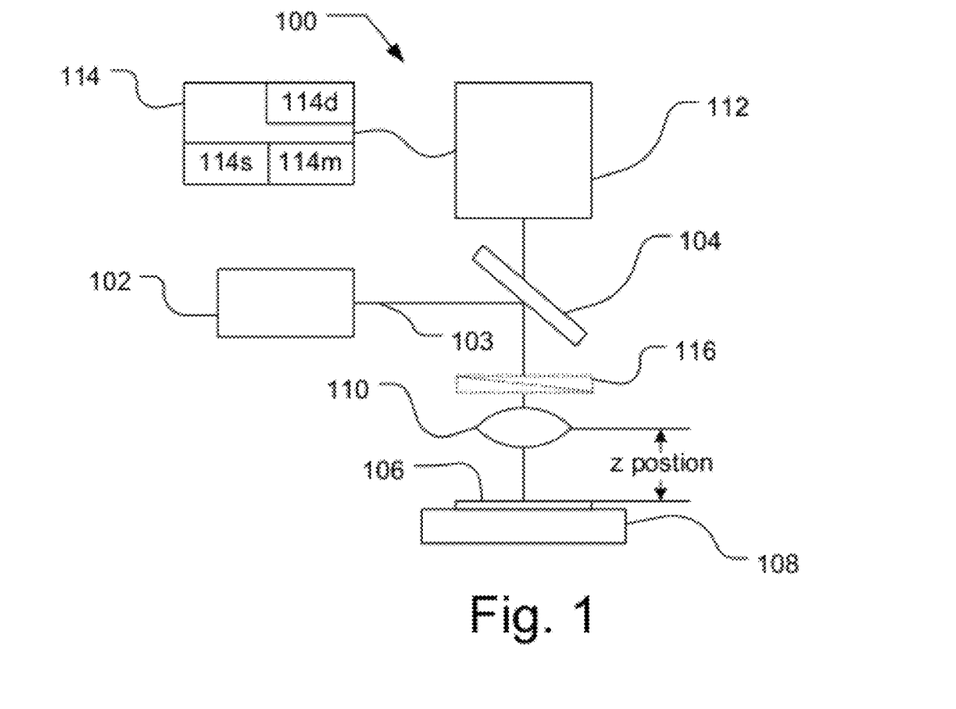
FIG. 1 illustrates an optical metrology system, such as a spectroscopic reflectometer, that may be used in accordance with an embodiment of the present invention.

FIG. 1 illustrates an optical metrology system 100, such as a spectroscopic reflectometer, that may be used in accordance with an embodiment of the present invention. The metrology system 100 includes a polychromatic light source 102 (or sources) that generates a sample beam 103 that is partially reflected by beam splitter 104 towards the sample 106. Sample 106 may be, e.g., a semiconductor wafer or flat panel display or any other substrate, and is supported by a stage 108, which may be a polar coordinate, i.e., R-θ, stage or an x-y translation stage. The stage 108 is also capable of motion in the vertical direction, known as the z direction. The sample beam 103 is focused onto the sample 106 by a dispersive optical system, such as a refractive objective lens (or series of lenses) 110. The dispersive optical system may include refracting and/or diffracting optical elements. The beam is reflected off the sample 106 and the reflected light is transmitted through the lens 110 and a portion of the reflected light is transmitted through beam splitter 104 to be received by a spectrophotometer 112. Spectrophotometer 112 is coupled to processor 114 that includes a computer-readable storage medium 114s or memory storing a computer program executable by the computer, which analyzes the data provided by spectrophotometer 112. The processor 114 may also be used to control the data acquisition and analysis of metrology system 100 as described herein. The processor 114 may store the final or one or more preliminary results in a storage medium 114m or display the results with a user interface device 114d, such as a display or printer.

It should be understood that the metrology system 100 may include additional elements, such as one or more polarizing elements, e.g., illustrated with broken lines 116, and imaging systems. Moreover, while metrology system 100 is illustrated in FIG. 1 as a reflectometer, other types of metrology devices, such as spectroscopic ellipsometers, profilometers, or other spectroscopic devices may be used in accordance with an embodiment of the present invention. The metrology system 100 may move the sample 106, i.e., via stage 108, relative to objective lens 110 and/or move the objective lens 110 or the entire optical system relative to the sample 106 to adjust the focus.

Figure 2:
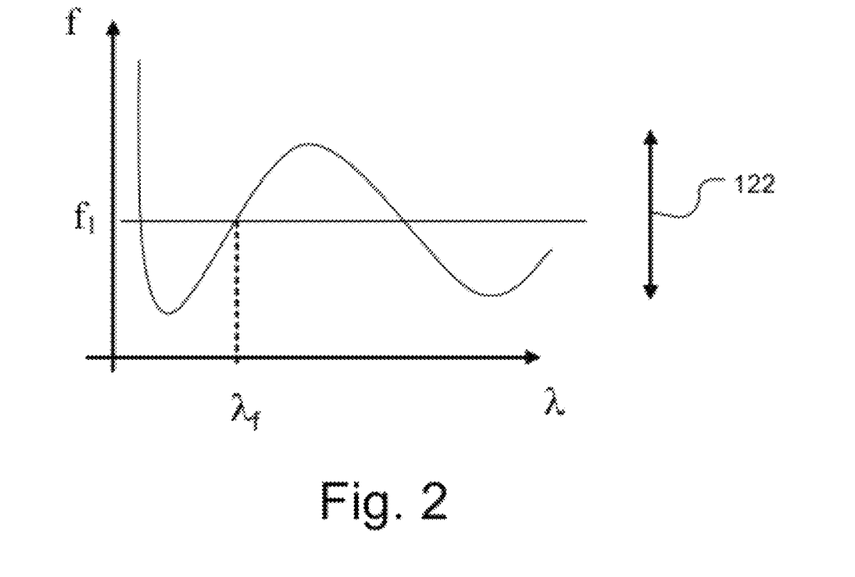
FIG. 2 illustrates an example of the relationship between wavelength ($\lambda$) and the focal length (f) of a typical dispersive optical system.

The focal length of dispersive optics are a function of wavelength. FIG. 2 illustrates, by way of example, the relationship of wavelength ($\lambda$) and the focal length (f) of a multi-element refracting lens. As can be seen in FIG. 2, the focal length (f) varies as a function of wavelength (x). Accordingly, when a metrology system, such as system 100 shown in FIG. 1, holds the sample 106 during measurement at a set vertical distance (z position) from the objective lens 110, only a few wavelengths $\lambda$ will be in focus, meaning that only a few wavelengths have the smallest possible spot size and the maximum intensity. While three wavelengths are shown as in focus in FIG. 2, the number of wavelengths in focus will depend on the type of optical system.

During a conventional focusing process of a metrology system, the system will place the sample at a z position that coincides with the focus position of a particular wavelength $\lambda_f$, e.g., at position $f_1$ in FIG. 2. In systems with conventional focusing systems, the distance between the sample and lens is held at that z position. However, at that z position, only one or a few wavelengths in the measurement spectrum are actually in focus. Additionally, the sensitivity to variations in the sample position is also a function of wavelength. Typically, but not always, wavelengths close to the focal wavelength $\lambda_f$ show less sensitivity to small changes of the z position of the sample than wavelengths that are farther away from the focal wavelength $\lambda_f$. Due to limited repeatability of focusing methods, a variation in z-position results in systematic errors in the measured intensity spectra.

Figure 3:
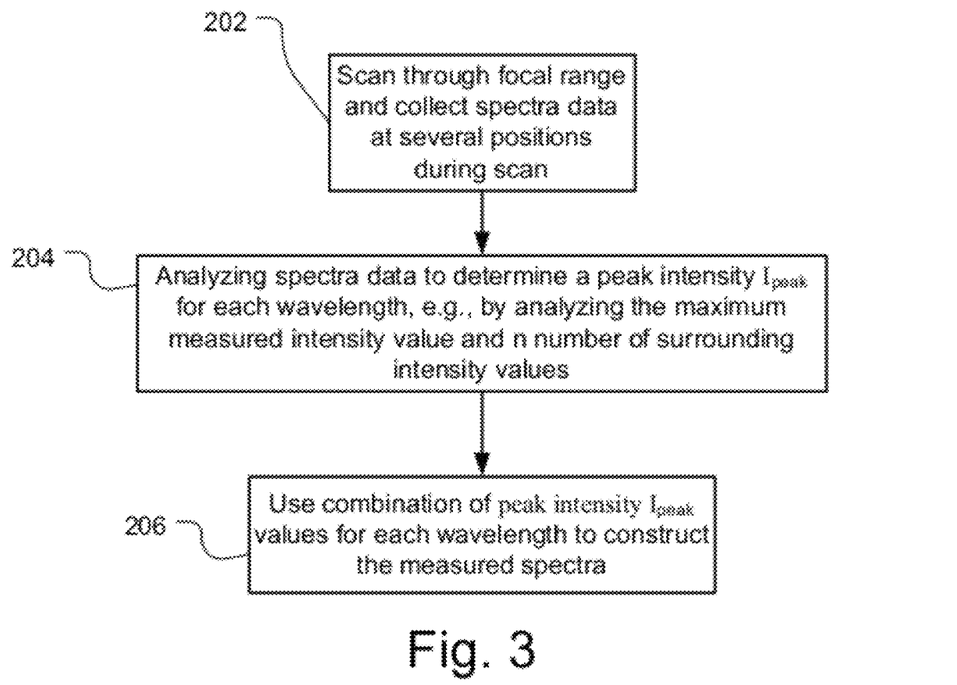
FIG. 3 is a flow chart illustrating the operation of a metrology system, in accordance with an embodiment of the present invention.

FIG. 3 is a flow chart illustrating the operation of a metrology system, in accordance with an embodiment of the present invention. As will be seen, a metrology system operating in accordance with an embodiment of the present invention does not require a focusing process prior to measuring the sample, as described above, but will increase the precision and repeatability of the measurement by decreasing the systematic noise component.

As shown in block 202, during the measurement of the sample, the distance between the sample 106 and the objective lens 110 is not held at one z position, but instead the metrology system 100 varies the distance between the sample 106 and objective lens to scan through the focal range of the dispersive optical system, e.g., objective lens 110, as illustrated by arrow 122 in FIG. 2. By way of example, the focal range may be 150 μm depending on the optical system. In some embodiments, the scan may be greater than the focal range of the optical element in order to allow fitting for the maximum intensity for wavelengths with focal positions on the edge of the range, as well as in order to account for slight sample position variations in the z direction. The scan through the focal range may be achieved by moving the sample 106, via stage 108 relative to the objective lens 110 and/or moving the objective lens 110 or the optical system relative to the sample 106. While scanning through the focal range, the metrology system 100 collects the spectral data at a plurality of z positions as shown in block 202. In other words, the intensity values are recorded along with the associated z-positions for a plurality of wavelengths, e.g., in storage medium 114m (FIG. 1), as illustrated by a single wavelength in FIG. 4, discussed below. It should be understood that while the present disclosure discusses intensity values, other measurements quantities, such as polarization state, may be used instead of intensity values with the present invention. The spectral data may be collected while continuously scanning, e.g., at a constant speed, through the range of z positions or while holding the sample at a series of discrete positions within the range of z positions. In one embodiment, the z positions at which the spectral data is collected are equally spaced.

The spectral data is then analyzed to determine the peak intensity $I_{peak}$ for each wavelength as shown in block 204. As is well known in the art, a spectrophotometer has a finite wavelength resolution that corresponds to the size of the pixels in the detector array, along with size of the entrance slit and the wavelength range of the spectrophotometer. Thus, while each datum point in the spectral data is actually composed of intensity versus a small range of wavelengths (the finite wavelength resolution as described above), the range of wavelengths is conventionally referred to by a single wavelength value, e.g., the center wavelength or a wavelength that has a whole number wavelength that falls within the pixel. Accordingly, it should be understood that the term "wavelength" is used herein to include a range of wavelengths that is detected in one or more pixels by a conventional finite resolution spectrophotometer. Moreover, it should be understood that the range of wavelengths may be detected in consecutive or non-consecutive pixels in the spectrophotometer.

Figure 4:
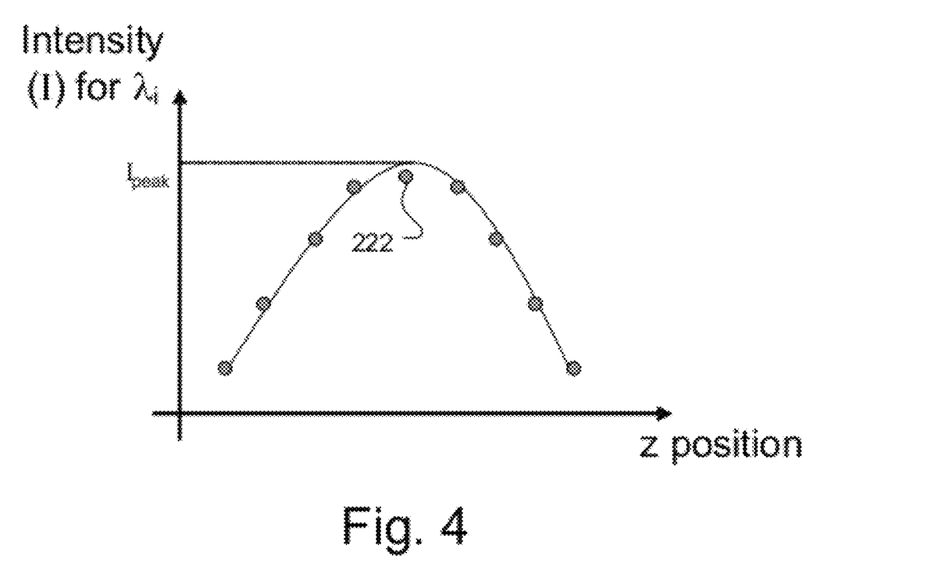
FIG. 4 is a graph illustrating an example of the measured intensity (I) values at different z positions for a single wavelength $\lambda_i$.

FIG. 4 is a graph illustrating an example of the measured intensity (I) values at different z positions for a single wavelength $\lambda_i$. In one embodiment, the peak intensity $I_{peak}$ is determined using the maximum measured intensity value (data point 222) and a number n of measured intensity values around the maximum measured intensity value. By way of example, the peak intensity $I_{peak}$ may be determined by curve fitting the maximum measured intensity value (data point 222) and a number n of measured intensity values and locating the peak of the curve, as illustrated in FIG. 4. Commonly used fitting algorithms that may be used include, e.g., Gaussian, quadratic, polynomial or non-linear regression, least-squares fitting, or Levenberg-Marquardt. Thus, as illustrated in FIG. 4, the peak intensity $I_{peak}$ may not necessarily coincide with the maximum measured intensity value 222.

Figure 5A:
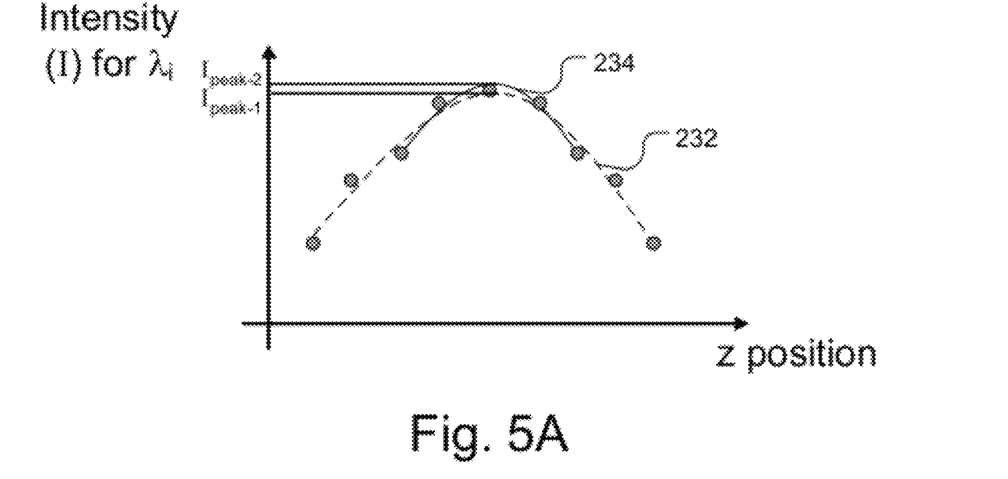
FIGS. 5A and 5B illustrate measured intensity values and spot size, respectively, as a function of focal position (z position) at a wavelength $\lambda_i$.
Figure 5B:
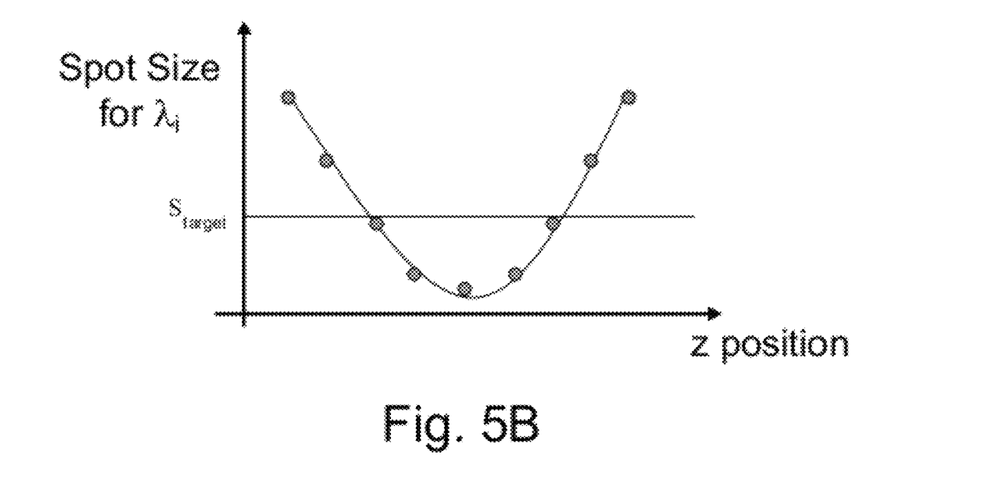

In one embodiment, the number n of intensity values from block 204 is varied from wavelength to wavelength in order to optimize the overall spot size of the system while optimizing the measurement precision. The number n of intensity values used to determine the peak intensity $I_{peak}$ directly impacts the effective spot size. FIGS. 5A and 5B illustrate measured intensity values and spot size, respectively, as a function of focal position (z position) at a wavelength $\lambda_i$. As can be seen in FIGS. 5A and 5B, the intensity and spot size are, in general, inversely correlated. FIGS. 5A and 5B illustrate the effect of including the measured intensity values from z positions that produce a spot size that is larger than the target size in the determination of the peak intensity $I_{peak}$.

By way of example, the sample target may have a limited size, illustrated by line $S_{target}$ in FIG. 5B. The properties of the target may be significantly different from the surroundings of the target, as illustrated by the intensity values shown in FIG. 5A. Data that is collected while the spot size is larger than the target size will include information that is external to the target is illustrated in FIG. 5B as data points above the line $S_{target}$. Using all the acquired data points (i.e., n=8), illustrated by the dotted line 232 in FIG. 5A, will generate a peak intensity $I_{peak-1}$ that includes information from outside the target. However, by reducing the number n of intensity values (i.e., n=4), a different curve fit is generated, illustrated by solid line 234, and information external to the target is excluded. Accordingly, a more accurate peak intensity $I_{peak-2}$ for the target is derived.

Thus, by varying the number n of intensity values around the maximum measured intensity to determine the peak intensity $I_{peak}$ for different wavelengths, the effective spot size can be controlled. The number n of intensity values around the maximum measured intensity required for different spot sizes at each wavelength may be determined prior to the measurement process, e.g., during calibration of the metrology system, and stored in a look up table or the like, to be used during measurement.

In other embodiments, the spectral data may be analyzed (block 204 in FIG. 3) to determine the peak intensity $I_{peak}$ in manners other than curve fitting. For example, the peak intensity $I_{peak}$ may be derived by determining the maximum measured intensity value 222 and using that value as the peak intensity $I_{peak}$ for wavelength $\lambda_i$, which is equivalent to curve fitting as described above and holding the number n to zero. Using the maximum measured intensity value 222 as the peak intensity $I_{peak}$ may be particularly acceptable when spectral data is collected at many z positions. Alternatively, the spectral data may be statistically analyzed to determine the peak intensity $I_{peak}$. For example, an average, weighted average, or other appropriate statistical technique may be used with a number or all of the measured intensity values to derive a value for the peak intensity $I_{peak}$. In such an embodiment, it may be possible for the derived value of the peak intensity $I_{peak}$ to be less than the maximum measured intensity value 222. Nevertheless, because the derived peak intensity $I_{peak}$ is a function of the measured intensity values at multiple z positions, and the peak intensities for other wavelengths are similarly determined, such a derived peak intensity $I_{peak}$ may still be useful.

As described in block 204 in FIG. 3, the peak intensity $I_{peak}$ is determined for each desired wavelength $\lambda$. The combination of the peak intensity $I_{peak}$ values for a plurality or all of the wavelengths of interest is then used to construct the measured spectrum for the sample, e.g., and stored in storage medium 114m (FIG. 1), as shown in block 206 in FIG. 3. The measured spectrum may be referred to herein as a constructed spectrum or generated spectrum. The measured spectrum, which consists of the peak intensity $I_{peak}$ values, can then be used to determine the sample properties in a conventional manner, including using known referencing techniques, which can then be stored in storage medium 114m or displayed with user interface 114d (FIG. 1).

Accordingly, the conventional focusing process is eliminated with the present invention, which improves the move-acquire-measure time. Further improvements of throughput may be obtained, with an embodiment of the present invention, through the use of available focal information, e.g., from the video focus during calibration, to minimize the focal scan range, i.e., scanning through the focal range near the approximate focal position determined from the available focal information, as opposed to scanning through the extremes of the focal range. The present invention similarly eliminates the necessity of moving the aperture, which is commonly performed in conventional focusing systems. For example, in certain type of measurements smaller numerical apertures are desirable, while the accuracy and repeatability of conventional focusing processes is generally improved by using the largest possible numerical aperture. Therefore in metrology systems with conventional focusing systems, an aperture is introduced to reduce the numerical aperture when performing a measurement and that aperture is removed during the conventional focusing process. With the present invention, the step of moving the aperture between focusing and measurement can be eliminated.

In addition, with the present invention, multiple measurements with focusing in between each measurement are not necessary with the present invention, which improves throughput of the metrology. Multiple measurements are typically used in metrology systems with conventional focusing systems in order to reduce the systematic errors in the measured intensity spectra introduced by repeatability errors in the focusing. Moreover, the present invention is intrinsically focus insensitive allowing the use of higher NA optics, which may allow measurements of smaller targets. Because each wavelength in the measured spectrum in accordance with the present invention is at the optimum focal position, the spot size for each wavelength is minimized and the intensity for each wavelength is maximized.

Figure 6A:
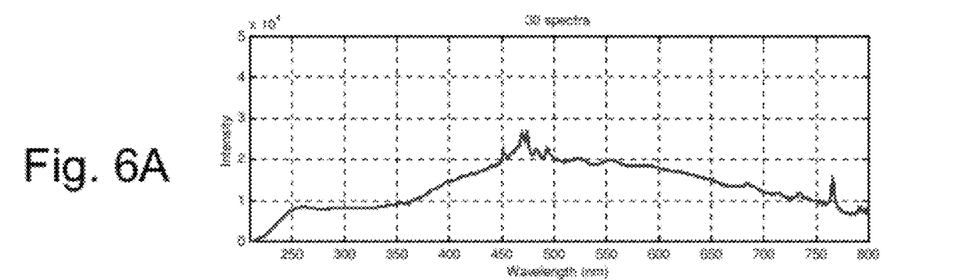
FIG. 6A is a graph showing spectra (intensity vs. wavelength) collected from a sample, in accordance with an embodiment of the present invention
Figure 6B:
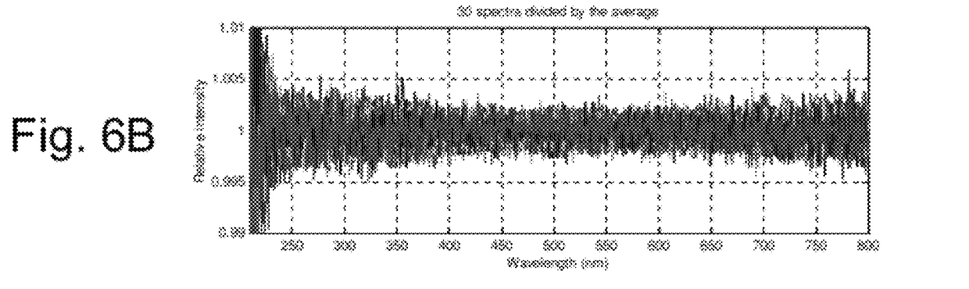
FIG. 6B illustrates the noise in the spectra of FIG. 6A.

FIG. 6A shows the measured spectra (intensity vs. wavelength) for a sample of native $SiO_2$ on Si. The measured spectra of FIG. 6A is actually 30 measured spectra, each of which is a combination of peak intensities determined in accordance with an embodiment of the present invention, as described above. The data used to determine the peak intensities to produce each of the measured spectra was collected for 16 ms at fifteen discrete z positions while the optical system scanned through the focal range. FIG. 6B illustrates the noise of the measured spectra of FIG. 6A, by dividing the 30 measured spectra by the average intensity. As illustrated in FIG. 6B, the noise in the measured spectra of FIG. 6A appears randomly distributed and is therefore independent of focus.

Figure 7A:
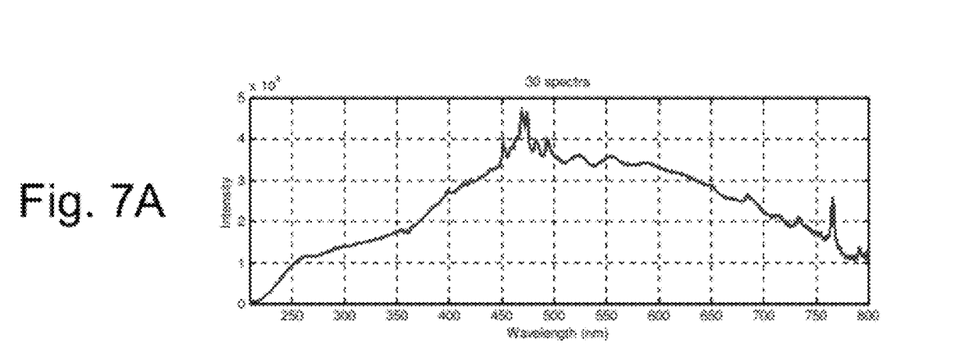
FIG. 7A is a graph showing the spectra (intensity vs. wavelength) collected from a sample with an optical system using a conventional focusing process
Figure 7B:
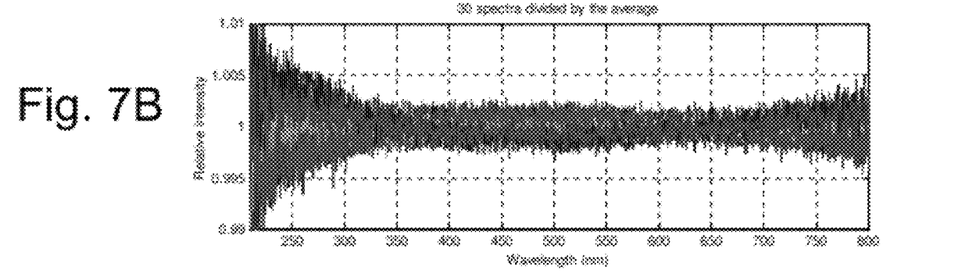
FIG. 7B illustrates the noise in the spectra of FIG. 7A.

FIG. 7A, by way of comparison, shows the spectra (intensity vs. wavelength) collected from the same sample with the same optical system used to generate the data of FIG. 6A, but using a conventional focusing and data acquisition process. The spectra of FIG. 7A is actually 30 spectra each of which was obtained after a separate conventional focusing process. Each of the 30 spectra is an average of eight 40 ms collections from the detector. The effective integration for the spectra shown in FIG. 7A is approximately the same as the effective integration of the 6A shown above. FIG. 7B illustrates the noise of the spectra of FIG. 7A by dividing the 30 spectra by the average intensity. As illustrated in FIG. 7B, the noise is dominated by the systematic error introduced by the focus positioning error.

Figure 8A:
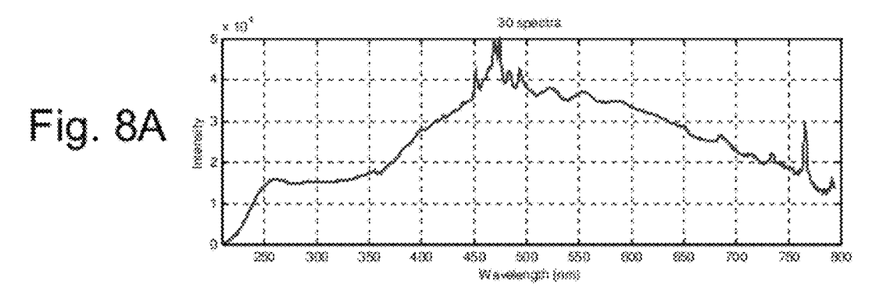
FIG. 8A is a graph showing spectra (intensity vs. wavelength) collected from a sample, in accordance with an embodiment of the present invention
Figure 8B:
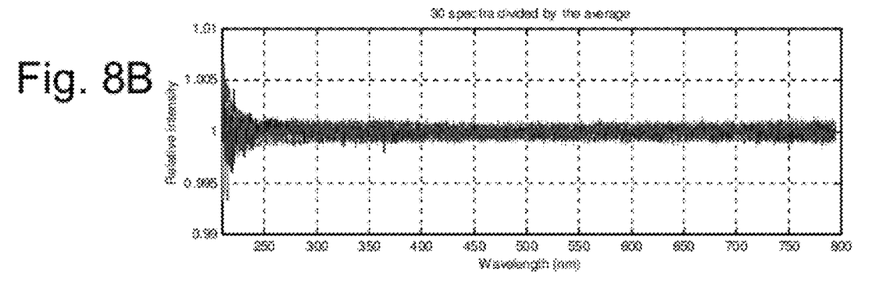
FIG. 8B illustrates the noise in the spectra of FIG. 8A.

FIG. 8A shows the measured spectra for the sample derived in a manner similar to that described in FIG. 6A above. The measured spectra in FIG. 8A is again actually 30 measured spectra, each of which is a combination of peak intensities determined in accordance with an embodiment of the present invention. Unlike the data obtained for FIG. 6A, however, the data used to determine the peak intensities that produced each of the measured spectra of FIG. 8A was obtained using long data collection for increased precision. The data was obtained as an average of eight 40 ms collections from the detector made at fifteen discrete z positions while the optical system scanned through the focal range. FIG. 8B illustrates the noise of the measured spectra of FIG. 8A, by dividing the 30 measured spectra by the average intensity. As can be seen in the FIG. 8B, the remaining noise appears to be random and is therefore independent of focus.

Figure 9A:
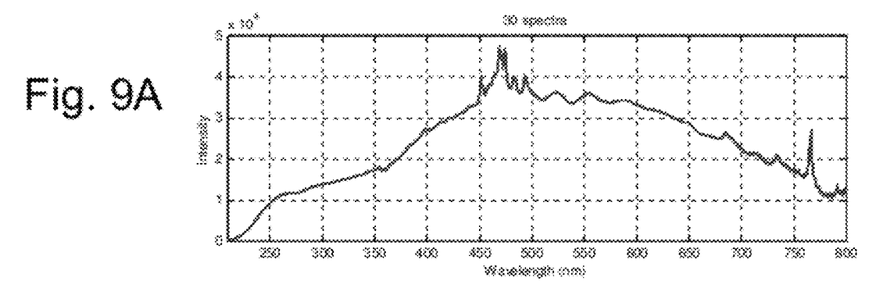
FIG. 9A is a graph showing the spectra (intensity vs. wavelength) collected from a sample with an optical system using a conventional focusing process
Figure 9B:
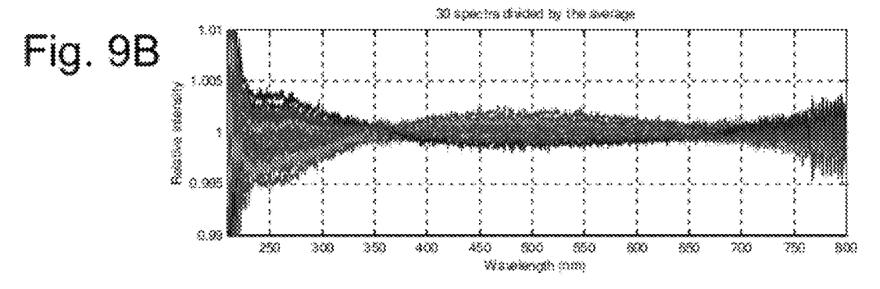
FIG. 9B illustrates the noise in the spectra of FIG. 9A.

FIG. 9A, by way of comparison to FIG. 8A, shows the spectra conventionally collected from the sample. The spectra in FIG. 9A is again 30 spectra, each of which was obtained after a conventional focusing process. Each of the 30 spectra is an average of 120 40 ms collections from the detector. The effective integration for the spectra shown in FIG. 9A is approximately the same as the effective integration of the 8A shown above. FIG. 9B illustrates the noise of the spectra of FIG. 7A by dividing the 30 spectra by the average intensity. Again, as illustrated in FIG. 9B, the noise is still dominated by the systematic error introduced by the focus positioning error.

In an embodiment in which one or more polarizing elements are used with the metrology system 100, the measured spectra may be generated as described in reference to FIG. 3, for each position of the polarizing element. For example, where the polarizing element 116 is positioned in a TE and TM orientation with respect to a diffracting sample, two separate measured spectra will be generated, each being a collection of theoretical peak intensities $i_{peak}$. If the polarizing element 116 is continuously rotating, a plurality of scans through the focal range is performed, with the scanning through the focal range and the rotation of the polarizing element 116 synchronized such that at multiple polarization positions there is full spectral data at several z positions. Alternatively, the spectral data may be collected at discrete steps during the scan through the focal range, with the polarizing element 116 rotating at each discrete step, or at discrete steps of the rotation of the polarizing element 116 while continuously scanning through the focal range.

In addition, the present invention may be used with oblique angle measurements, such as that performed by a spectroscopic ellipsometer. In one embodiment, the scan through the focal range may be combined with a scan along the horizontal direction, i.e., the x direction, of the sample and the detector so that the measurement spot is held at the same measurement location on the sample. In addition, as described above, the rotation of the polarizing element in the spectroscopic ellipsometer may be synchronized with the scanning of the focal range and multiple scans performed to produce full spectral data for multiple polarization positions at multiple z positions. In another embodiment, a spectroscopic ellipsometer may employ discrete steps in the focal range while rotating the polarizing element or, alternatively, employ discrete steps in the polarizing element position while continuously scanning the focal range.

Figure 10:
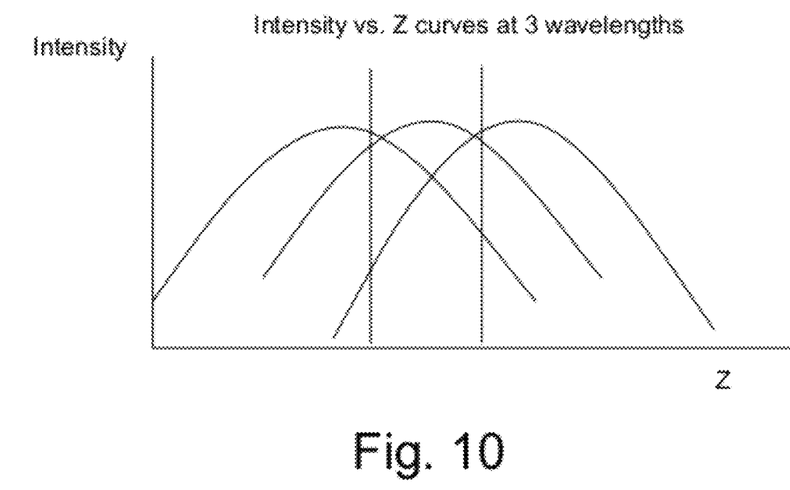
FIG. 10 illustrates intensity vs. Z curves at three wavelengths, where the data is measured at two discrete Z positions, illustrated by the vertical lines.

Additionally, scanning a large Z range, or stepping to many Z positions, takes time. It is not always necessary to scan through the peak intensity at each wavelength. By way of example, FIG. 10 illustrates intensity vs. Z curves at three wavelengths, where the data is measured at two discrete Z positions, illustrated by the vertical lines. On each curve there are two data points, one for each Z position. With knowledge of the mathematical formula describing the shape of the curve (e.g., from a previous calibration step which scanned the full range), then the rest of the curve, including the peak intensity, can be calculated based on the two data points. Depending on the complexity of the mathematical formula, more than two points may be needed. For example, for a parabola, two points are needed. For a more complicated curve, more Z positions will be needed. During measurement, the Z height may be moved to discrete positions and stopped before acquiring spectra, or the Z may be moved continuously while acquiring spectra.

Figure 11:
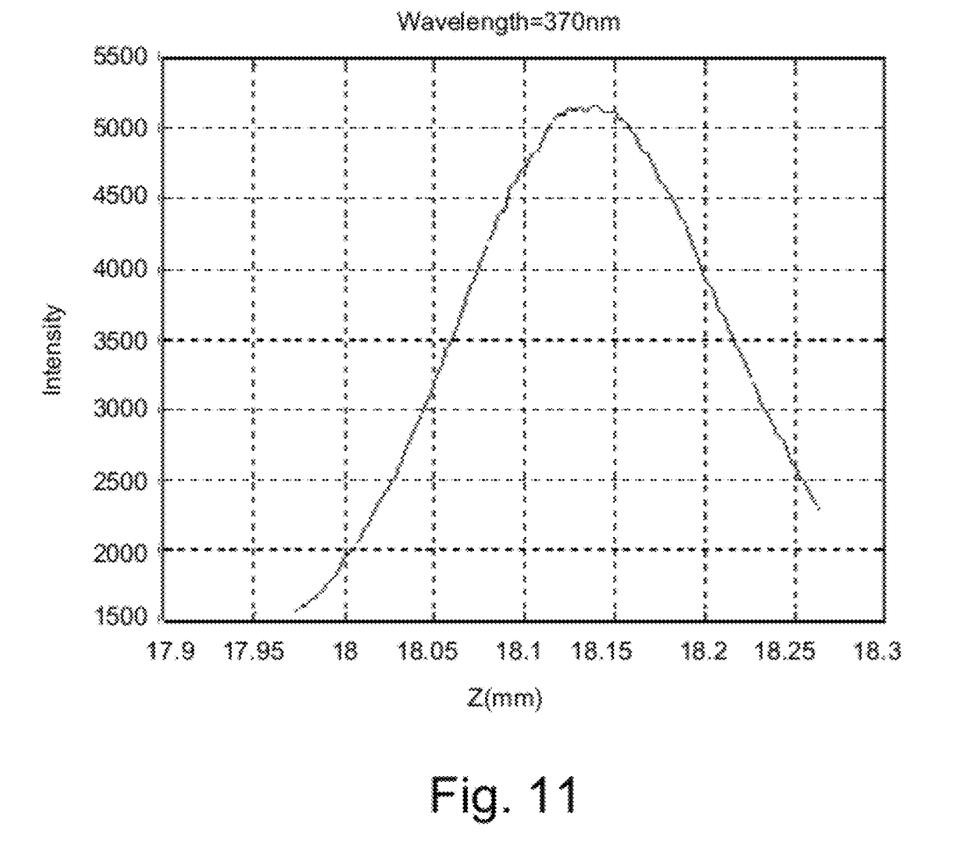
FIG. 11 illustrates a detected intensity vs Z (focus) curve for a single wavelength.
Figure 12:
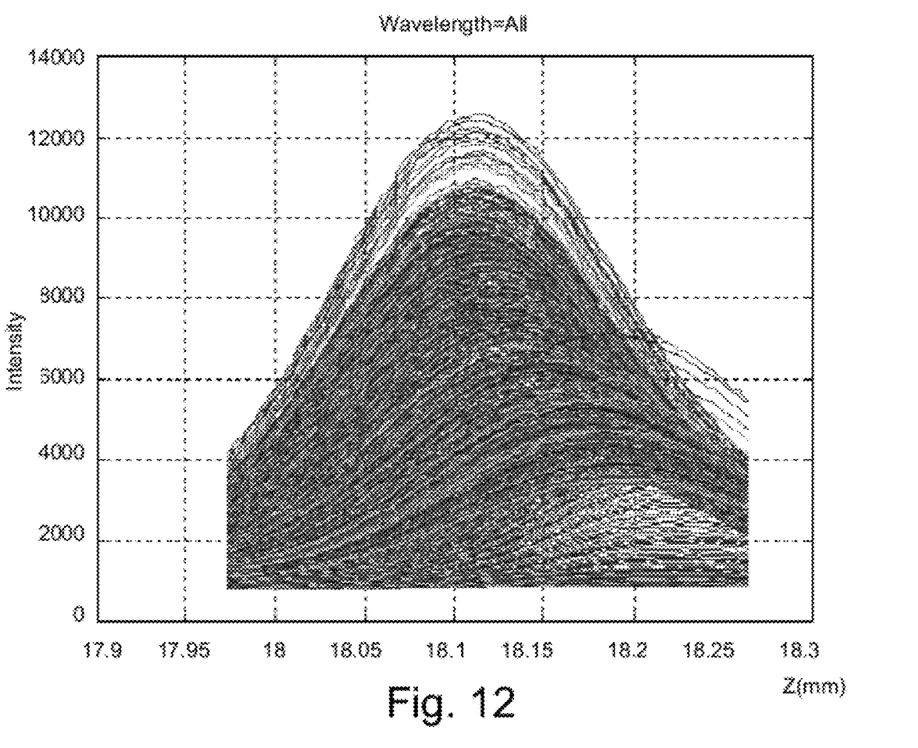
FIG. 12 illustrates detected intensity vs Z (focus) curves for a plurality of wavelengths.
Figure 13:
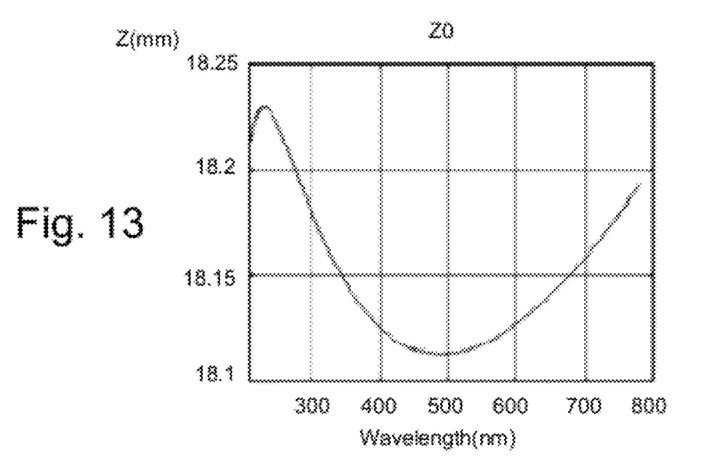
FIG. 13 illustrates a curve for the best Z as a function of wavelength.

By way of example, a detected intensity vs Z (focus) curve for a single wavelength may appear as shown in FIG. 11. Of course, different wavelengths have different peak intensities and because of the axial chromatic aberration of the optical system, the peak intensities of different wavelengths may be at different Z positions. FIG. 12 illustrates an example of the detected intensity vs Z (focus) curves for all wavelengths. Calculating the best Z as a function of wavelength, e.g., using the curves shown in FIG. 12, will produce a curve as shown in FIG. 13, which is sometimes referred to as a Lens Calibration curve.

The intensity vs Z curve from each wavelength, e.g., as shown in FIG. 11 is composed of discrete points, but a curve may be fit to the data. For example, a Gaussian may work well for curve fitting. The optical metrology system 100 may be calibrated by performing a scan through the Z heights, fitting a Gaussian (or other appropriate curve) and saving the fit parameters in a calibration file. Accordingly, during measurement, one data point on the curve may be acquired and used along with the fit parameters to calculate the best Z position and the corresponding peak intensity $I_{peak}$. Therefore, a wafer may be loaded, the focus height set to one Z position, one spectrometer scan acquired, and the best Z positions and the corresponding peak intensities $I_{peak}$ for each desired wavelength may be determined, which may then be combined to construct the measured spectra (as discussed in 206 of FIG. 3).

If, however, the next sample has a different reflectance, the curve will be scaled up or down according to the different reflectance. Accordingly, knowing only one point on the curve may not provide enough information to reconstruct the curve. Thus, the spectrum may be collected at two or more Z positions. Now, for each wavelength, there are two or more data points on the curve, which is enough information to reconstruct the curve, and calculate both the best Z, and the corresponding peak intensity at each desired wavelength. As illustrated in FIG. 10, however, the collected data may be acquired at Z positions only on one side of the peak intensity or on either side of the peak intensity. If desired, the Z values can be used to focus the system, or the determined peak intensities $I_{peak}$ for each desired wavelength may be combined to construct the measured spectra (as discussed in 206 of FIG. 3). Which method is used will depend on the various errors in the measurement.

In practice, some Z positions may produce data points that are too far from the best Z (i.e., peak intensity) to provide a good fit for all wavelengths. In other words, the peak Z and/or peak intensity found from the extrapolated fit may not be precise for all wavelengths if a small number of Z positions are used to acquire data. The Z and intensity values may only be accurate at a few wavelengths. Thus, the spectrum may be measured at additional Z positions to provide more data, at the expense of speed. With better calibration data, i.e., the better the chosen mathematical function fits the data, the fewer Z positions will be needed.

Additionally, the shape of the Z vs wavelength curve is known from the lens calibration procedure. The Z vs. wavelength curve is generally very accurate because the sample has been scanned over a range which encompasses all the peak intensity values, and there are enough data points on the sides of the curves to provide a very accurate fit to the data. Thus, the Z vs wavelength cuve shape may be fit to the acquired data points during measurement to reduce the noise. With the shape of the Z vs wavelength curve known, the best Z at any wavelength can then be calculated. This is useful because it may be desired to focus the sample at a specific wavelength.

Additionally, if desired, rather than using polychromatic light, monochromatic light may be used. With monochromatic light, the data is still collected from the sample at a plurality of focal positions and a peak value is determined based on the collected data. The characteristic of the sample can then be determined based on the peak value. Alternatively, a characteristics, such as the best focal position may be determined.

Although the present invention is illustrated in connection with specific embodiments for instructional purposes, the present invention is not limited thereto. For example, while the present disclosure discusses refractive optics, the present invention may be used with other dispersive optical systems including diffractive optical elements. Various adaptations and modifications may be made without departing from the scope of the invention. Therefore, the spirit and scope of the appended claims should not be limited to the foregoing description.

What is claimed is:

1. A method of measuring a characteristic of a sample using light that interacts with the sample and is detected from which data is collected, the method comprising:
   collecting data from the sample at a plurality of focal positions;
   determining a peak value based on the collected data from only one side of the peak value; and
   determining the characteristic of the sample based on the peak value.

2. The method of claim 1, wherein the light is polychromatic light, the collected data is spectral data, and determining a peak value comprises determining a peak value for each of a plurality of wavelengths in the polychromatic light based on the collected spectral data, the method further comprising generating a spectrum using the determined peak value for each of the plurality of wavelengths, and wherein determining the characteristic of the sample based on the peak value comprises determining the characteristic of the sample based on the generated spectrum.

3. The method of claim 2, wherein each peak value is a peak intensity value.

4. The method of claim 2, wherein each peak value is determined using at least one of curve fitting and a statistical analysis.

5. The method of claim 2, wherein each peak value is determined using the maximum measured value, and a statistical analysis.

6. The method of claim 2, wherein collecting spectral data from the sample at a plurality of focal positions comprises storing a plurality of data points for each wavelength, wherein determining a peak value for each of a plurality of wavelengths comprises using different numbers of data points for at least two different wavelengths.

7. The method of claim 2, the spectral data is collected using an optical system having color dispersive characteristics.

8. The method of claim 7, wherein the optical system having color dispersive characteristics comprises at least one of a refractive objective lens and a diffractive optical element.

9. The method of claim 2, wherein collecting spectral data from the sample at a plurality of focal positions in the range of focal positions for the polychromatic light comprises varying a distance along an optical path between the sample and at least one component in an optical system used to collect the spectral data.

10. The method of claim 2, wherein the spectral data includes intensity values.

11. The method of claim 2, further comprising storing or displaying the determined characteristic of the sample.

12. The method of claim 1, wherein the collected data includes data on both sides of the peak value.

13. The method of claim 1, wherein the peak value is determined by curve fitting.

14. The method of claim 13, further comprising calibrating the shape of the curve prior to curve fitting.

15. A method of measuring a characteristic of a sample using monochromatic light that interacts with the sample and is detected from which data is collected, the method comprising: collecting data from the sample using the monochromatic light at a plurality of focal positions; determining a peak value based on the collected data; and determining the characteristic of the sample based on the peak value, wherein the collected data includes data from only one side of the peak value.

16. The method of claim 15, wherein each peak value is a peak intensity value.

17. The method of claim 15, wherein each peak value is determined using at least one of curve fitting and a statistical analysis.

18. The method of claim 15, wherein each peak value is determined using the maximum measured value, and a statistical analysis.

19. The method of claim 15, wherein the collected data includes data on both sides of the peak value.

20. The method of claim 15, wherein the peak value is determined by curve fitting.

21. The method of claim 20, further comprising calibrating the shape of the curve prior to curve fitting.

* * * * *